(12) United States Patent
Prakash et al.

(10) Patent No.: US 6,872,855 B1
(45) Date of Patent: Mar. 29, 2005

(54) METHOD FOR EXPEDIENT SYNTHESIS OF [18F]-LABELED α-TRIFLUOROMETHYL KETONES

(75) Inventors: G. K. Surya Prakash, Hacienda Heights, CA (US); Mian M. Alauddin, Alhambra, CA (US); Jinbo Hu, Los Angeles, CA (US); Peter S. Conti, Pasadena, CA (US); George A. Olah, Beverly Hills, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 10/721,423

(22) Filed: Nov. 26, 2003

Related U.S. Application Data
(60) Provisional application No. 60/429,602, filed on Nov. 27, 2002.

(51) Int. Cl.[7] .......................... C07C 45/00; G21G 1/06; G06K 9/00
(52) U.S. Cl. ....................... 568/323; 568/325; 376/168; 382/130; 382/131
(58) Field of Search ................................ 568/323, 325; 376/168; 382/130, 131

(56) References Cited

U.S. PATENT DOCUMENTS
5,425,063 A  6/1995  Ferrieri et al. .............. 376/195

OTHER PUBLICATIONS

G.K. Surya Prakash, et al.; "Expedient synthesis of [$^{18}$F]-labeled α–trifluoromethyl ketones" Journal Of Labelled Compounds And Radiopharmaceuticals. J. Label Compd Radiopharm 2003; 46: 1087–1092.

Hideki Amii et al.; Mg°–promoted selective C–F bond cleavage of trifluoromethyl ketones: a convenient method for the systhesis of 2,2–difluoro enol silanes; Chem. Commun., 1999, 1323–1324.

G.K. Surya Prakash et al.; Facile preparation of di– and monofluoromethyl ketones from trifluoromethyl ketones via fluorinated enol silyl ethers; Journal of Fluorine chemistry 112 (2001) 357–362.

Synthetic and Medicinal Chemistry of Trifluoromethyl Ketones, Faculty of Pharmaceutical Sciences, Josai Univ., pp. 350–0295.

Michael H. Gelb et al.; "Fluoro Ketone Inhibitors of Hydrolytic Enzymes; Biochemistry", American Chemical Society, vol. 24, No., 8; Apr. 9, 1985; 1814–1817.

Lori H. Takahashi et al.; "Crystallographic Analysis of the INhibition of Procine Pancreatic Elastase by a Peptidyl Boronic Acit: Structure of a Reaction Intermediate; Biochemistry" American Chemical Society,1989, 28, 7610–7617.

Tina S. Morris et al.; In Vitro and Ex Vivo Inhibition of Hepatitis A Virus 3C Proteinase by a Peptidyl Monofluoromethyl Ketone; Bioorganic & Mecicinal Chemistry, vol. 5, No. 5, pp 797–807, 1997.

Barbara Imperiali et al.; Inhibition of Serine Proteases by Peptidyl Fluoromethyl Ketones; Biochemistry 1986, 25, 3760–3767

Masami Kawase et al.; "α–Trifluoromethylatec Acyloins Induced Apoptosis In Human Oral Tumor Cell Lines"; Bioorganic & Medicinal Chemistry Letters 9 (1999) 3113–3118.

Xavier Creary; "Reaction of Organometallic Reagents with Ethyl Trifluoroacetate and Diethyl Oxalate. Formation of Trifluoromethyl Ketones and αKeto Esters via Stable Tetrahedral Adducts"; J. Org. Chem 1987, 52, 5026–5030.

Takashi Keumi et al.; "A Convenient Trifluoroacetylation of Arenes with 2–(Trifluoroacetoxy)pyridine"; Chemistry Letters, pp. 783–786, 1990.

Jurgen Wiedemann et al.; Direct Preparation of Trifluoromethyl Ketones from Carboxylic Esters: Trifluoromethylation with (Trifluoromethyl)trimethylsilane; Anges. Chem. Int. Ed. 1998 37, No. 6, 820–821.

Rajendra P. Singh et al.; "Cesium Fluoride Catalyzed Trifluoromethylation of Esters, Aldehydes, and Ketones with (Trifluoromethyl)trimethylsilane"; J. Org. Chem. 1999, 64, 2873–2876.

G.K. Surya Prakash et al.; "A general method of halogenation for synthesis of αhalodifluoromethyl ketones and [$^{18}$]–labeled trifluoromethyl ketones"; Journal of Fluorine Chemistry 121 (2003) 239–243.

K. Uneyama et al, "Electroreductive Defluorination of Trifluoromethyl Ketones and Trifluoroacetic Acid Derivatives", Journal of Org. Chem., vol. 64, No. 18, pp. 6717–6723 (1999).

*Primary Examiner*—Johann Richter
*Assistant Examiner*—Sikarl A. Witherspoon
(74) *Attorney, Agent, or Firm*—Winston & Strawn LLP

(57) ABSTRACT

The present invention is directed to a convenient method of synthesizing radiolabeled α-trifluoromethyl ketones by a fluorination reaction. The present invention also relates to imaging agents and markers for identifying cell proliferation, or viral infection. The markers and imaging agents including the radiolabeled α-trifluoromethyl ketones that are prepared by the present method.

23 Claims, 3 Drawing Sheets

METHOD FOR EXPEDIENT SYNTHESIS OF [18F]-LABELED α-TRIFLUOROMETHYL KETONES

This application claims the benefit of provisional application No. 60/429,602 filed on Nov. 27, 2002, the content of which is incorporated herein by reference thereto.

FIELD OF THE INVENTION

This invention relates generally to a method for the synthesis of [$^{18}$F]-labeled trifluoromethyl ketones. The invention more particularly relates to a method for the synthesis of [$^{18}$F]-labeled trifluoromethyl ketones by [$^{18}$F]-labeled fluorination of 2,2-difluoroenol silyl ethers.

BACKGROUND ART

There has been increasing interest in biologically active compounds known as α-Trifluoromethyl ketones (TFMKs). It has been found that many TFMK compounds have unique properties due to its α-trifluoromethyl ketone functionality. In example, TFMK's have been found to be potential hydrolytic enzyme inhibitors. In particular, TFMK's have been found to be inhibitors of protease.

Kawase has reported that the trifluoromethyl group in the α-position of the carbonyl of the TFMK facilitates the formation of tetrahedral hemiketals or hydrates with water. The hydrated molecule interacts with protease, and inhibits the enzyme activity Kawase, M. *J. Syn. Org. Chem. Jpn.* 2001, 59, 755, which is incorporated herein by reference thereto.

It has also been demonstrated that TFMK's are cytotoxic agents against human oral tumor cell lines, such as human squamous carcinoma cells HSC-2 and salivary gland tumor cells HSG. Kawase, M.; Sakagami, H.; Kusama, K, Motohashi, N.; Saito, S. *Bioorg. Med. Chem. Lett.* 1999, 9, 3113, incorporated herein by reference.

Traditionally, TFMKs are prepared from inexpensive trifluoroacetic acid derivatives. See, Creary, X. *J. Org. Chem.* 1987, 52, 5026; Keumi, T.; Shimada M.; Takahashi, M.; Kitajama, H. Chem. Lett. 1990, 783. Both of which are incorporated herein by reference. Additionally, the present inventors have recently reported the direct preparation of TFMKs from carboxylic esters with (trifluoromethyl) trimethylsilane (TMS-CF$_3$). See, Wiedemann, J.; Heiner, T.; Mloston, G.; Prakash, G. K. S.; Olah, G. A. *Angew. Chem. Ant. Ed.* 1998, 37, 820, which is incorporated herein by reference thereto.

Our reported method has been extended by others with CsF catalyzed trifluoromethylation of esters. Most recently we have developed a simple and convenient general synthesis of α-trifluoromethyl ketones by fluorination using elemental fluorine F$_2$ (Prakash, G. K S.; Hu, J.; Alauddin, M. M.; Conti, P. S.; Olah, G. A. *J Fluorine Chem.* 2003, 121, 239, incorporated herein by reference thereto.

There is a need for an expedient process for radioactive labeling of TFMKs. However, the current synthesis methods are not suitable for the synthesis of [$^{18}$F]-labeled TFMKs since it is difficult to prepare [$^{18}$F]-labeled trifluoroacetic acid derivatives or TMS-CF$_3$ due to the short half-life of $^{18}$F ($t_{1/2}$=110 min).

SUMMARY OF THE INVENTION

The aforementioned need has been satisfied by the present invention which discloses the first synthesis of [$^{18}$F]-labeled TFMKs by fluorination of 2,2-difluoro silyl enol ethers with radioactive fluorine [$^{18}$F]-F$_2$.

The present invention is preferably directed to an expedient method for synthesizing [$^{18}$F]-labeled trifluoromethyl ketones from the fluorination of silyl enol ethers. Thus, it has now been discovered that TFMK compounds have the potential for radiolabeling with fluorine-18. Advantageously, the radiolabeled compounds can be used as markers for identification of cell proliferation, markers for identification of viral infection, or for PET imaging.

In accordance with the present invention, a method of synthesizing [$^{18}$F]-labeled α-trifluoromethyl ketones is provided by reacting [$^{18}$F]-F$_2$ under sufficient reaction conditions with a compound having the general formula 1, wherein R refers to an alkyl having 1 to 24 carbons or an aryl group having 6 to 24 carbon atoms.

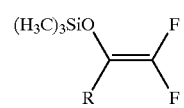

1

In one aspect of the invention, the alkyl or aryl group includes a ring. In another aspect of the invention, the alkyl group is substituted with at least one halogen, nitro group, or alkoxy group. In yet another aspect of the invention, the alkoxy group has one to eight carbon atoms. In another aspect of the invention, the alkoxy group is substituted with at least one substituent including an alkyl group having 1 to 8 carbon atoms, a halogen, an amino group, or any combination thereof. Advantageously, the substituent does not participate in the reaction.

In a preferred embodiment, the method further comprises dissolving the silyl ether compound in acetonitrile to form a solution; cooling the solution to about −50° to about −15° C.; preparing a mixture of [$^{18/19}$F]-F$_2$ and nitrogen; and bubbling the mixture of [$^{18/19}$F]-F$_2$ and nitrogen into the solution for about 5 to 15 minutes to form a reaction mixture. [$^{18/19}$F]-F$_2$ can be prepared by bombardment with [$^{18}$O]O$_2$ in a cyclotron and mixing with non-radioactive F$_2$.

The silyl ether is preferably 2,2-difluoroenol silyl ether and may be prepared by mixing magnesium, tetrahydrofuran, and chlorotrimethylsilane to form a reactant mixture; cooling the mixture to between about −15° C. to 5° C.; adding trifluoroacetophenone to the cooled mixture, and stirring the mixture for about 0.5 to 1.5 hours to produce the difluoroenol silyl ether.

The [$^{18}$F]-labeled trifluoromethylketones that are synthesized generally have a radiochemical purity greater than 99% and specific activities between about 15 to 20 GBq/mmol at the end of synthesis. They are produced at yields of between about 45 to 55%.

Several [$^{18}$F]-labeled α-trifluoromethyl ketones have been synthesized by the present method. Compounds 2a~2d shown below have been successfully synthesized in accordance with the method of the invention.

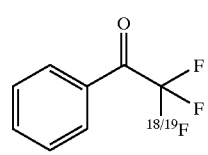

2a

2b

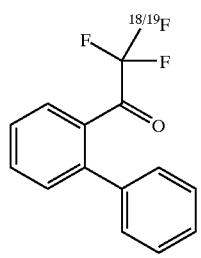

2c

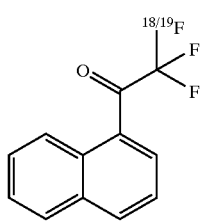

2d

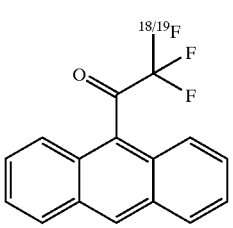

Also in accordance with the present invention is an imaging agent comprising the [$^{18}$F]-labeled α-trifluoromethyl ketones synthesized from the method of the invention. In one aspect of the invention, the imaging agent is useful for positron emission tomography (PET) imaging.

The invention also relates to a marker that can be used for detecting cell proliferation or for detecting viral infection. The marker of the invention comprises the [$^{18}$F]-labeled α-trifluoromethyl ketones synthesized according to the method of the invention and preferably includes those having a radiochemical purity of about 99%.

BRIEF DESCRIPTION OF THE DRAWINGS

The invention is better understood by reference to the drawings figures, wherein.

DETAILED DESCRIPTION OF THE PREFERRED EMBODIMENTS

Figure 1:
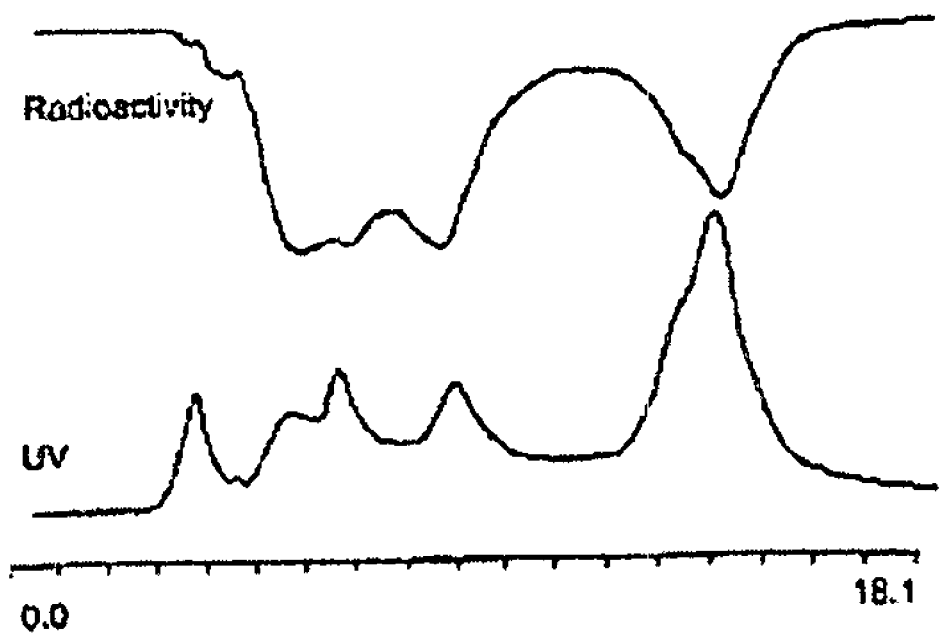
FIG. 1 illustrates a chromatogram of purified labeled trifluoromethyl ketones.

The present invention relates to a general and expedient method for the preparation of [$^{18}$F]-labeled trifluoromethyl ketones. In accordance with the method of the invention, a fluorination reaction between [$^{18}$F]-labeled F$_2$ and 2,2-difluoroenol silyl ether 1 produces [$^{18}$F]-labeled trifluoromethyl ketones 2 as shown below. The R group of 2,2-difluoroenol silyl ethers 1 preferably include an alkyl or aryl group.

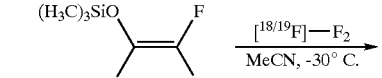

1

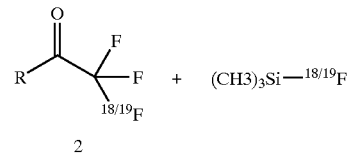

2

As noted above, radiolabeled trifluoromethyl ketone compounds 2a~2d, shown below, have been successfully synthesized in accordance with the method of the invention.

2a

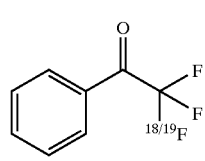

2b

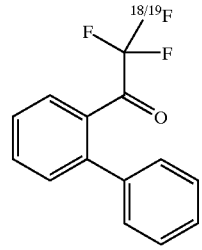

2c

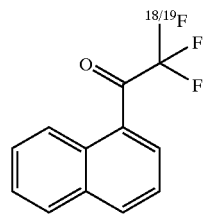

2d

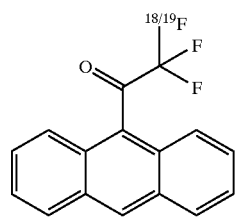

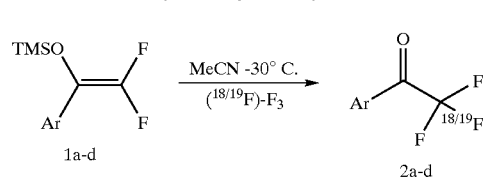

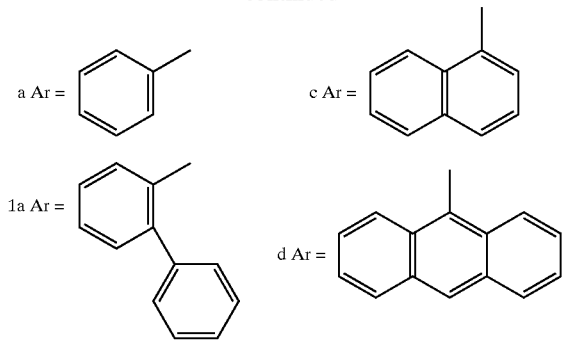

In accordance with one aspect of the invention, difluoroenol silyl ether compounds 2a–d, shown above, can be prepared from a mixture of compound 1, which is shown below, TMSCl, and Mg[11] in anhydrous THF or DMF. The mixture is stirred for about 15 to 30 minutes, preferably 20 minutes, at a temperature between about −10° C. to about 5° C., and preferably at 0° C.

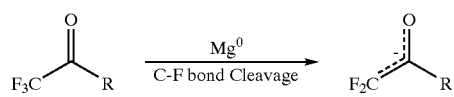

Difluoroenol silyl ether is obtained after filtration. The R of compound 1 includes but is not limited to Ph, 4-MeOC$_6$H$_4$, 4-CF$_3$C$_6$H$_4$, 4-ClC$_6$H$_4$, 2-furyl, 2-thienyl, C$_6$H$_{13}$, or Cy. The method is disclosed in Amii, H.; Kobayashi, T.; Hatamoto, Y.; Uneyama, K. *Chem. Comm.* 1999, 1323, the entire content of which is expressly incorporated herein by reference. Preferably, tetrabutylammonium fluoride with D$_2$O is added to the THF or DMF for the preparation of the difluoro enol silyl ethers, as disclosed in Prakash, G. K. S.; Hu, J.; Olah, G. A. *J Fluorine Chem.* 2001, 112, 357), the entire content of which is expressly incorporated herein by reference. It has been found that silyl enol ethers produced by this preferred method have greater stability for hydrolysis compared to other silyl enol ethers. Although the stability of the silyl ethers enable simple handling without decomposition, freshly prepared compounds were used for radiolabeling experiments.

The goal compounds, [$^{18}$F]-labeled trifluoromethyl ketones, were prepared by fluorination of 2,2-difluoroenol silyl ethers 1 with [$^{18/19}$F]-F$_2$. The [$^{18/19}$F]-F$_2$ was produced in the cyclotron by bombardment of [$^{18}$O]O$_2$ followed by mixing the target gas with non-radioactive F$_2$. The mixture of [$^{18/19}$F]-F$_2$ was bubbled into the solution of the substrates 2,2-difluoroenol silyl ethers at low temperature for efficient trapping of activity. Trapping of activity was quite efficient for 2–3 mg (~10 μmol) of the precursors. Since the syntheses were carrier added, a sufficient amount of F$_2$ was present, resulting in absence of any unreacted starting material in the reaction mixture.

Reactions of 2,2-difluoro-1-aryl-1-trimethylsiloxyethenes with [$^{18}$F]-F$_2$ at low temperature produced [$^{18}$F]-labeled α-trifluoromethyl ketones. The radiolabeled products were isolated by purification with column chromatography in 22–28% yields, and were decay corrected (d. c.) in 3 runs per compound. The radiochemical purity was greater than 99%, with specific activities of 15–20 GBq/mmol at the end of synthesis (EOS). The synthesis time was 35–40 min from the end of bombardment (EOB). This one step simple method is highly useful for the radiochemical synthesis of potential biologically active [$^{18}$F]-labeled α-trifluoromethyl ketones for PET.

Trifluoromethyl ketones can form hydrated products in the presence of water which can cause difficulties during HPLC purification using MeCN/H2O solvent system. However, compound 2c was found to be relatively stable in aqueous system during HPLC purification and pure product was isolated in good yield (54%). Referring to FIG. 1, purification of 2c is represented by a chromatogram. The desired product was eluted in 13 to 15 minutes, which could then be isolated in pure form.

Figure 2:
FIG. 2 illustrates a HPLC chromatogram of a labeled trifluoromethyl ketone.

Referring to FIG. 2, analysis of pure product 2c by HPLC showed two radioactive and three UV active peaks. The UV peaks compared to the hydrated product (a), partial hydrated product (b), and trifluoromethyl ketone (c). Only two radioactive peaks were observed corresponding to the hydrated product (a) and the ketone (c) and the ratio between the ketone and hydrated product was approximately 10:90.

In order to verify the reactivity of the trifluoromethyl ketones with water a pure 18F-labeled product collected by HPLC in CH3CN/water was heated for a short time of 1 to 2 minutes. Analysis of the product by either HPLC and TLC demonstrated 100% hydrated compound.

Although the other radiolabeled ketones could not be purified by HPLC since the products readily converted to the hydrated compound and eluted much earlier than the desired ketones, the radiolabeled ketones were in fact purified by chromatography on a small silica gel column and eluted with the organic solvent mixture, ethyl acetate and hexane (10:90). Fractions (0.5 mL) of the product were collected and radioactivity was measured on a dose calibrator. The products were eluted in the earlier fractions with an r.f. value of approximately 0.8. Pure fractions after combining were analyzed by TLC and found to be co-eluted with authentic sample checked by both UV and radioactivity.

Figure 3:
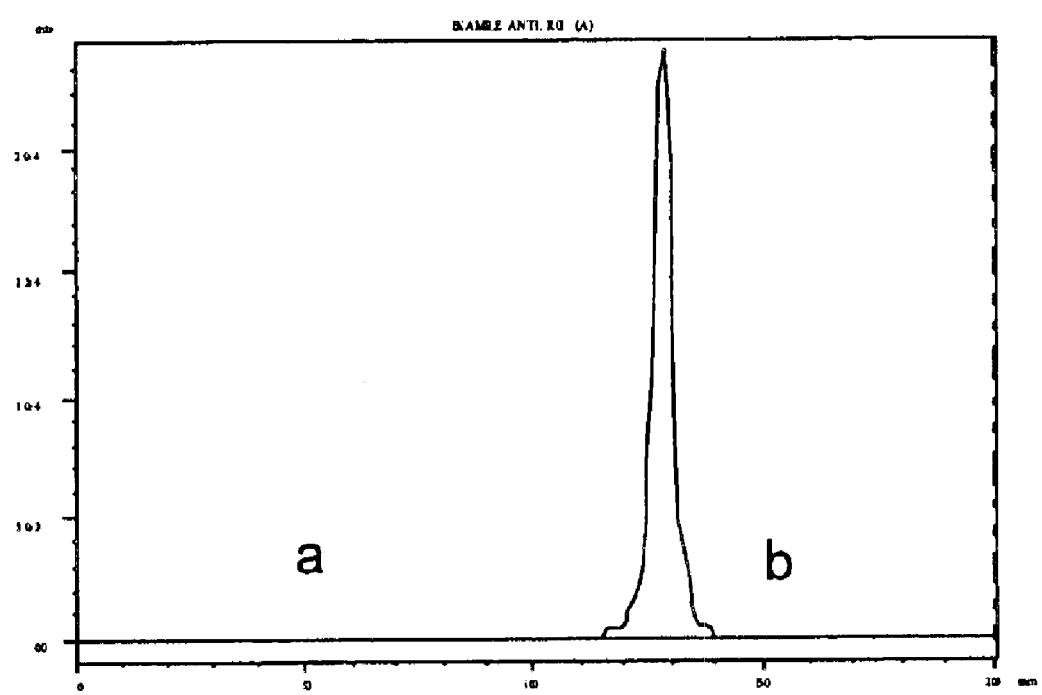
FIG. 3 illustrates a radio TLC of a labeled trifuoromethyl ketone of the invention.

Referring to FIG. 3 illustrated is a representative radio TLC for the compound 2b where a is the point of application and b is the solvent front.

In non-radioactive preparations excess F$_2$ was used and the chemical yields were greater than 80%. However, in the radiochemical syntheses only 50% of the activity is incorporated into the substrate resulting lower yields in the range of 22–28% (d. c.) from the EOB. The radiochemical purity was greater than 99% with specific activities of 15–20 GBq/mmol. The synthesis time was 35–40 min from the EOB. In a representative preparation of 2b, 30 mCi of labeled product was obtained starting from 120 mCi of trapped activity [$^{18}$F]-F$_2$.

The present invention will be further understood by the examples set forth below, which are provided for purpose of illustration and not limitation.

EXAMPLES

In the following examples, all reagents and solvents were purchased from Aldrich Chemical Co. (Milwaukee, Wis.), and used without further purification, unless otherwise specified. Dichloromethane (CH$_2$Cl$_2$) and fluorotrichloromethane (CFCl$_3$) were distilled over calcium hydride (CaH$_2$), and acetonitrile (MeCN) was distilled over phosphorus pentoxide (P$_2$O$_5$) prior to use.

$^1$H, $^{13}$C and $^{19}$F NMR spectra were recorded on a Bruker 500 or 360 MHz NMR spectrometer in chloroform-D using tetramethysilane and trichlorofluoromethane as internal standards, respectively. Mass spectra were obtained on a Hewlett Packard 5890 Gas Chromatograph equipped with a Hewlett Packard 5971 Mass Selective Detector.

Column chromatography was performed using silica gel (60–200 mesh) and ethyl acetate/hexane (10:90) as eluent. Thin layer chromatography (TLC) was performed on a silica gel plate (1×10 cm) and developed in the appropriate solvent system ethyl acetate/hexane (10:90). Radioactivity on the developed TLC plate was scanned on a TLC scanner (Bioscan Inc., Washington D.C.) to obtain a radiochromatogram.

Example 1

Preparation of 2.2-difluoroenol silyl ethers (1–d)

2,2-difluoroenol silyl ethers (1-d) were prepared from their respective ketones by magnesium metal mediated reductive defluorination.

To a dry 250 ml Schlenk flask the following compounds were added: magnesium turnings (1.45 g, 60 mmol), dry tetrahydrofuran (THF, 120 ml) and chlorotrimethylsilane (TMSCl, 13.0 g, 120 mmol). The flask was cooled to 0° C. 2,2,2-Trifluoroacetophenone (non-radioactive) 2a (5.2 g, 30 mmol) was added drop wise into the flask with a syringe. After addition of the 2,2,2-Trifluoroacetophenone, the reaction mixture was stirred for an additional 1 h. The completion of the reaction was monitored by $^{19}$F NMR spectroscopy. The solvent and excess TMSCl were removed under vacuum, and hexane (50 ml) was added to the residue. Solid impurities were removed by suction filtration, and the solvent was evaporated to yield 2,2-difluoro-1-phenyl-1-trimethylsiloxyethene 1a (6.8 g, 99% yield).

The product was characterized by $^{1}$H and $^{19}$F NMR spectroscopy and mass spectrometry. Spectroscopic data were consistent with the literature for 2,2-difluoro-1-phenyl-1-trimethylsiloxyethene. $^{1}$H NMR: δ=0.60 (s, 9H), 7.38 (t, J=7.5 Hz, 1H), 7.47 (t, J=7.5 Hz, 2H), 7.61 (d, J=8.8 Hz, 2H); $^{13}$C NMR: δ=0.02, 114.09 (q, $^{2}J_{C-F}$=18.0 Hz), 125.84, 127.72, 128.25, 132.71, 154.87 (t, $^{1}J_{C-F}$=286.8 Hz); $^{19}$F NMR: δ=100.39 (d, $^{2}J_{F-F}$=68.0 Hz), -112.16 (d, $^{2}J_{F-F}$=68.0 Hz). MS(70 eV, m/z): 228 (M$^{+}$), 213, 197, 186 (, 177, 131, 115, 105, 89, 81, 77, 73.

Compounds having the formulae 1b–d were also characterized by $^{1}$H and $^{19}$F NMR spectroscopy and mass spectrometry.

Example 2

Preparation of [$^{18}$F]-α-trifluoromethyl ketones (2a–d)

Experiments were performed under similar conditions as described in Example 1.

2,2-Difluoro-1-phenyl-1-trimethylsiloxy-ethene 1a (2 μL, 11 μmol) was dissolved in dry acetonitrile (0.5 ml) and cooled to −45° C. A mixture of fluorine [$^{18/19}$F]-F$_2$ and nitrogen (F$_2$/N$_2$ (v/v=⅛)) was bubbled into the solution for 10 min. Radioactivity was measured on a dose calibrator (Capintec Inc., Ramsey, N.J.), and the reaction mixture was warmed to room temperature.

The crude product was purified by chromatography on a silica gel column using 10% ethyl acetate in hexane as eluent. Fractions (0.5 mL) were collected and radioactivity was measured. Fractions containing radioactivity were combined and solvent was evaporated to obtain the pure product. The product was analyzed by TLC with an authentic compound as a reference. The TLC plate after development was scanned for radioactivity on a TLC scanner, checked under UV lamp and compared with the reference compound. Analysis of the TLC plate showed the material to be 99% pure. Radiochemical yield was 22% (d. c).

Compounds 2b–d were produced in similar radiochemical yields in the range of 22–28% (d. c).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, and or methods of use of the invention, can be made without departing from the spirit and scope thereof.

What is claimed is:

1. A method for the synthesis of [$^{18}$F]-labeled trifluoromethylketones comprising the steps of
reacting [$^{18}$F]-F$_2$ with a silyl ether compound having the general formula 1

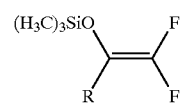

wherein R refers to an alkyl group having between 1 and 24 carbon atoms or an aryl group having between 6 and 24 carbon atoms under reaction conditions sufficient to form a [$^{18}$F]-labeled trifluoromethylketone.

2. The method of claim 1, wherein the alkyl or the aryl group comprises a ring.

3. The method of claim 1, wherein the alkyl group is substituted with at least one halogen, nitro, or alkoxy group.

4. The method of claim 3, wherein the alkoxy group has one to eight carbon atoms.

5. The method of claim 3, wherein the substituent does not participate in the reaction.

6. The method of claim 3, wherein the alkoxy is substituted with at least one substituents selected from the group consisting of an alkyl group having between 1 and 8 carbon atoms, a halogen, and an amino group, or any combination thereof.

7. The method of claim 1, wherein the condition sufficient to form a [$^{18}$F]-labeled trifluoromethylketone include a reaction temperature of between about −50° C. to about −15° C.

8. The method of claim 1, wherein the [$^{18/19}$F]-F$_2$ is prepared by bombardment with [$^{18}$O]O$_2$ in a cyclotron and mixing with non-radioactive F$_2$.

9. The method of claim 1, wherein the [$^{18}$F]-F$_2$ mixture is bubbled into a solution comprising silyl ether compounds for about 5 to 15 minutes.

10. The method of claim 1, wherein the silyl ether is 2,2-difluoroenol silyl ether and further wherein the 2,2-difluoroenol silyl ether is prepared by:
mixing magnesium, tetrahydrofuran, and chlorotrimethylsilane to form a reactant mixture;
cooling the mixture to between about −15° C. to 5° C.;
adding trifluoroacetophenone to the cooled mixture; and
stirring the mixture for about 0.5 to 1.5 hours to produce the difluoroenol silyl ether.

11. The method of claim 10, wherein the difluroenol silyl ether is 2,2-difluoro-1-phenyl-1-trimethylsiloxy-ethene.

12. The method of claim 1, which further comprises:
dissolving the silyl ether compound in acetonitrile to form a solution;
cooling the solution to about −50° to about −15° C.;
preparing a mixture of [$^{18/19}$F]-F$_2$ and nitrogen; and
bubbling the mixture of [$^{18/19}$F]-F$_2$ and nitrogen into the solution for about 5 to 15 minutes to form a reaction mixture.

13. The method of claim 1, wherein the [$^{18}$F]-labeled trifluoromethylketones synthesized have a radiochemical purity greater than 99%.

14. The method of claim 1, wherein the [$^{18}$F]-labeled trifluoromethylketones that are synthesized have specific activities between about 15 to 20 GBq/mmol at the end of synthesis.

15. The method of claim 1, wherein the radiochemical yields of the [$^{18}$F]-labeled trifluoromethylketones are between about 45 to 55%.

16. The method of claim 1, wherein the [$^{18}$F]-labeled trifluoromethylketones synthesized has the following general formula 2a.

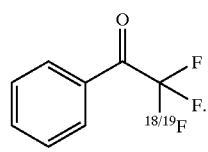

2a

17. The method of claim 1, wherein the [$^{18}$F]-labeled trifluoromethylketones synthesized has the following general formula 2b.

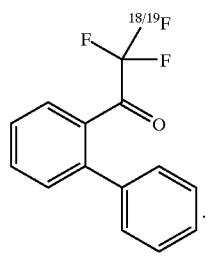

2b

18. The method of claim 1, wherein the [$^{18}$F]-labeled trifluoromethylketones synthesized has the following general formula 2c.

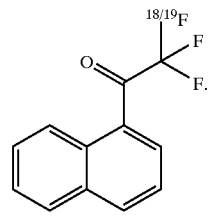

2c

19. The method of claim 1, wherein the [$^{18}$F]-labeled trifluoromethylketones synthesized has the following general formula 2d.

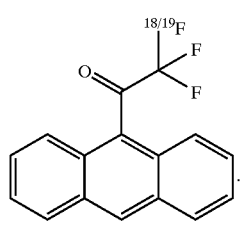

2d

20. An imaging agent comprising the [$^{18}$F]-labeled trifluoromethyl ketone of claim 1.

21. The imaging agent of claim 20, having a radiochemical purity of about 99% for use in positron emission tomography.

22. A marker for detecting cell proliferation or viral infections comprising the [$^{18}$F]-labeled trifluoromethyl ketone of claim 1.

23. The marker of claim 22, having a radiochemical purity of about 99%.

* * * * *

UNITED STATES PATENT AND TRADEMARK OFFICE
CERTIFICATE OF CORRECTION

PATENT NO. : 6,872,855 B1
DATED : March 29, 2005
INVENTOR(S) : Prakash et al.

Page 1 of 1

It is certified that error appears in the above-identified patent and that said Letters Patent is hereby corrected as shown below:

Title page,
Item [56], References Cited, OTHER PUBLICATIONS,
"Hideki Amii et al." reference, change "$Mg^0$-promoted" to -- $Mg^0$-promoted --; and change "systhesis" to -- synthesis --.
"Michael H. Gelb et al." reference, delete ""Fluoro Ketone Inhibitors of Hydrolytic Enzymes; Biochemistry", American Chemical Society," and insert -- "Fluoro Ketone Inhibitors of Hydrolytic Enzymes," Biochemistry, --.
"Lori H. Takahaski et al." reference, delete ""Crystallographic Analysis of the INhibition of Procine Pancreatic Elastase by a Peptidyl Boronic Acit: Structure of a Reaction Intermediate; Biochemistry" American Chemical Society, 1989, 28, 7610-7617" and insert -- "Crystallographic Analysis of the Inhibition of Porcine Pancreatic Elastase by a Peptidyl Boronic Acid: Structure of a Reaction Intermediate," Biochemistry, 1998, 28, 7610-7617 --.
"Tina S. Morris et al" reference, change "Bioorganic & Mecicinal Chemistry" to -- Bioorganic & Medicinal Chemistry --.
"Masami Kawase et al." reference, change "α-Trifluoromethylatec Acyloins Induced" to -- α-Trifluoromethylated Acyloins Induce --.
"Xaier Creary" reference, change "αKeto" to -- α-Keto --.
"Jurgen Wiedemann et al." reference, change "Agnes. Chem. Int. Ed." to -- Agnew. Chem Int. Ed. --.
"G.K. Surya Prakash et al." reference, change "α-halodifluoromethyl ketones and [18]-labeled" to -- α-halodifluoromethyl ketones and [18F]-labeled --.

Signed and Sealed this

Nineteenth Day of July, 2005

JON W. DUDAS
*Director of the United States Patent and Trademark Office*